United States Patent [19]

Worrell et al.

[11] 4,350,828

[45] Sep. 21, 1982

[54] CRYSTALLIZATION OF ISOPHTHALIC ACID

[75] Inventors: G. Richard Worrell; Alan R. Hirsig, both of Media, Pa.

[73] Assignee: Atlantic Richfield Company, Los Angeles, Calif.

[21] Appl. No.: 264,776

[22] Filed: May 18, 1981

Related U.S. Application Data

[63] Continuation of Ser. No. 164,472, Jun. 30, 1980, abandoned.

[51] Int. Cl.³ .................... C07C 51/42; C07C 51/16
[52] U.S. Cl. ................................ 562/486; 562/412
[58] Field of Search ............................. 562/486, 412

[56] References Cited

U.S. PATENT DOCUMENTS 3,917,681 11/1975 Shinn et al. .................... 562/486

Primary Examiner—Alan Siegel

[57] ABSTRACT

A filter cake of crude isophthalic acid is dispersed as a slurry in acetic acid, and thereafter heated to a temperature bringing about the dissolving of the isophthalic acid. Such hot solution is subjected to very rapid evaporative crystallization in a single crystallization zone maintained at a pressure at which volatilization of the acetic acid occurs and at a temperature within the range of 180°–250° F., the heat input being controlled to promote such very rapid volatilization that more than half of the solvent quickly is volatilized. Moreover, more than half of the isophthalic acid content of the effluent is in the solids suspended in the slurry of such effluent. Because the volatilization is so rapid, only a relatively short residence time in the single crystallization zone is required for obtaining an effluent suitable for transfer to a separation zone. Isophthalic acid crystals are separated from the mother liquor in such separation zone. Such crystals are washed and dried to provide isophthalic acid having a purity and particle size distribution which are superior to typical prior commercial practice. Moreover, the yield is sufficiently to merit engineering approval in view of the simplicity of the process.

9 Claims, No Drawings

CRYSTALLIZATION OF ISOPHTHALIC ACID

RELATED APPLICATION

This is a continuation of Ser. No. 164,472 filed June 30, 1980, now abandoned.

FIELD OF INVENTION

This invention relates to the recrystallization of isophthalic acid to prepare an isophthalic acid having a particle size distribution which is commercially acceptable.

This invention relates to the preparation and purification of isophthalic acid. The invention also is concerned with the control of distribution of particle size during a crystallization step and to methods involving the continuous crystallization procedure having an advantageously short residence time in the crystallization zone.

PRIOR ART

Shinn et al U.S. Pat. No. 3,917,631 describes a method of recrystallizing isophthalic acid in a plurality of stages to prepare a product having an appropriate distribution of particle sizes. Such method has had significant commercial success. In the Example of Shinn et al, the one hour of first stage crystallization at 275° F. at 34 psia involves only minor volatilization of the solvent, so that the volume rate of the effluent is about 90% of the volume rate of the input. Crystallization by cooling is the significant feature of the 3 stage crystallization of the Example of Shinn et al. The cost for the equipment involved in such multi-stage recrystallization of Shinn et al as well as the operating costs for conducting the multi-stage crystallization, are sufficiently great that a continuing search for alternative approaches has been conducted in connection with plans for new plants for making IPA (i.e. isophthalic acid).

SUMMARY OF INVENTION

In accordance with a preferred embodiment of the present invention, a single stage of crystallization is conducted with rapid heat input to assure very rapid volatilization of the acetic acid solvent at a controlled temperature and at a controlled pressure for maintaining the vigorous boiling and rapid volatilizing action of the acetic acid, said controlled temperature being at least about 180° F. and not above about 250° F. The very rapid evaporative crystallization causes the high purity isophthalic acid crystals to form and to grow and to quickly provide an acceptable yield of solids in the slurry. Contrary to what would have been expected from the general teachings of prior literature concerning the 180°-250° F. range, the particle size distribution of the thus crystallized isophthalic acid is appropriate for commercial marketing of the isophthalic acid.

In preferred modifications of the invention, the crystallization is conducted on a continuous, as distinguished from a batch, basis. A crystallization zone is provided having the volume required for a controlled residence time. The hot solution of dissolved isophthalic acid is prepared in a dissolution zone at a controlled temperature and injected into liquid corresponding to that of crystallization maintained at a temperature at least 10° F. cooler than said dissolution zone. Such hot feed is injected into the slurry of the crystallization zone under conditions such that it is very promptly distributed throughout the crystallization zone. The rapid evaporation of a large amount of the acetic acid solvent from the crystallization zone provides a system in which substantially all of the isophthalic acid is precipitated as a slurry of crystals.

A stream of such slurry is withdrawn from the crystallization zone. Such slurry stream has a composition corresponding substantially to the average composition in the crystallization zone. The pounds per hour of isophthalic acid introduced through the hot stream corresponds accurately to the pounds per hour of isophthalic acid withdrawn in the slurry stream.

Most of the aqueous acetic acid solvent in the hot solution is volatilized in the single stage crystallization zone, so that only a minor amount of said solvent provides the liquid portion of the slurry. Of importance is the fact that substantially all of the undesired impurities remain in the liquid portion of the slurry and the fact that the suspended solids are purified phthalic acid crystals having a commercially acceptable range of particle sizes.

Such withdrawn slurry stream is subjected to a separation process such as filtration or centrifugation, thereby providing a filter cake containing the recoverable isophthalic acid. Such filter cake is washed with the aqueous acetic acid solvent and thereafter subjected to drying to provide an isophthalic acid product having a purity and distribution of particle sizes which are commercially acceptable.

The nature of the invention is further clarified by reference of a plurality of the examples.

EXAMPLES 1-2

An experimental apparatus featured a 500 ml autoclave as the single stage crystallization zone. A timer actuated discharge valve permitted pulses of stream of product to be withdrawn at a rate which controlled the residence time in the crystallization zone. The slurry withdrawn from such autoclave was directed to a vacuum filter for separation of the purified product from the filtrate.

Water circulated around the jacketed crystallization autoclave to provide the heat input for accelerating the rate of volatilization of the solution at the preselected temperature. A pressure relief system maintained an appropriate pressure in the crystallization zone for promoting such rapid volatilization of the solvent. Both the pressure and temperature in the dissolving zone were higher than in the crystallization zone. The hot solution was pumped from the dissolving zone to the crystallization zone at a rate such that the isophthalic acid input rate corresponded to the isophthalic discharge rate. A stirrer maintained uniform composition and uniform temperature of the slurry system throughout substantially all of the autoclave.

A first batch of crude product was processed through the dissolving zone, crystallization zone, and vacuum filter to evaluate the effect of variables such as evaporation rate, pressure, and temperature upon crystallization. Data concerning product purity for Controls A-G and Examples 1 and 2 are shown in Table 1.

Table 2 shows data concerning particle size distribution. It should be noted that the particle size distribution is significantly better for Example 2 than in Controls B, F, and G.

TABLE 1
CONTINUOUS RECRYSTALLIZATION OF ISOPHTHALIC ACID - PRODUCT ANALYSES

| Run No. Feed | Autoclave Temp., °F. | Average Crystallizer Residence Time, Min | PRODUCT ANALYSES | | | | | | | | | Calc. Recov. % |
|---|---|---|---|---|---|---|---|---|---|---|---|---|
| | | | MCBA ppm | MTA ppm | TPA % | OPA ppm | Total Unk, ppm | Absorbance 333 mu | 350 mu | $R_F/R_P$ MCBA | $R_F/R_P$ Unk | |
| A | 212 | 5 | 175 | <10 | <0.1 | <25 | 268 | 1.18 | 0.72 | 4.74 | 1.61 | 67 |
| 1 | 197 | 23 | 122 | <10 | <0.1 | <25 | 164 | 0.92 | 0.54 | 6.80 | 2.64 | 73 |
| B | 158 | 5 | 300 | 11 | <0.1 | 29 | 343 | 1.21 | 0.71 | 2.77 | 1.26 | 84 |
| C | 138 | 5 | 323 | 12 | <0.1 | <25 | 338 | 1.77 | 0.75 | 2.57 | 1.28 | 88 |
| D | 125 | 8.3 | 305 | <10 | <0.1 | 52 | 267 | 1.21 | 0.70 | 2.72 | 1.62 | 90 |
| E | 152 | 8.8 | 319 | 13 | <0.1 | <25 | 272 | 1.21 | 0.70 | 2.60 | 1.59 | 85 |
| F | 201 | 5 | 187 | <10 | <0.1 | <25 | 234 | 1.13 | 0.67 | 4.44 | 1.85 | 72 |
| 2 | 206 | 64 | 104 | <10 | | <25 | 165 | 0.94 | 0.58 | 7.98 | 2.62 | 70 |
| G | 152 | 85 | 229 | <10 | | <25 | 36.3 | 1.18 | 0.70 | 3.62 | 1.19 | 86 |

$R_F/R_P$ refers to ratio of feed to product concentrations

TABLE 2
PARTICLE SIZE ANALYSIS

| | Average microns | Retained on screen having microns of opening | B % | F % | 2 % | G % |
|---|---|---|---|---|---|---|
| Giant | 170 | 149 | 1.4 | 2.8 | 21.7 | 5.5 |
| Very large | 129.5 | 110 | 4.7 | 13.9 | 13.6 | 7.9 |
| Large | 92.5 | 75 | 14.1 | 20.6 | 21.8 | 14.8 |
| Big | | | 20.2 | 37.3 | 57.1 | 28.2 |
| Medium | 67.5 | 60 | 9.2 | 10.7 | 8.8 | 7.2 |
| Small | 52.5 | 45 | 12.8 | 14.4 | 10.8 | 11.6 |
| Intermediate | | | 22.0 | 25.1 | 19.6 | 18.8 |
| Very small | 37.5 | 30 | 11.5 | 13.6 | 7.9 | 10.6 |
| Dust | 25 | 20 | 17.1 | 10.0 | 7.5 | 16.4 |
| Fines | 10 | | 29.2 | 14.0 | 7.9 | 26.0 |
| | | | 57.8 | 37.6 | 23.3 | 43.0 |
| Total | | | 100.0 | 100.0 | 100.0 | 100.0 |

The purity of the product was subject to criticism in the Controls at temperatures below 180° F., as shown in Table 1. It is surprising that the purity should be greater when the crystallization is conducted at a higher temperature.

By a series of controls and examples, it is established that single stage crystallization of Isophthalic Acid should be conducted at a temperature within the range from 180° to 250° F. for a residence time within the range from 20 to 120 minutes while supplying sufficient heat to achieve within less than an hour the volatilization of most of the solvent and to provide a slurry in which at least 60% of the total isophthalic acid content is solid (as distinguished from dissolved) form.

EXAMPLE 3

A sample of isophthalic acid had the following composition:

| | |
|---|---|
| Isophthalic acid | about 97% |

TABLE 2
CONTINUOUS RECRYSTALLIZATION OF ISOPHTHALIC ACID - PRODUCT ANALYSES

| Run No. Feed | Autoclave Temp., °F. | Average Crystallizer Residence Time, Min | PRODUCT ANALYSES | | | | | | | | | | | Calc. Recov % |
|---|---|---|---|---|---|---|---|---|---|---|---|---|---|---|
| | | | MCBA ppm | MTA ppm | TPA % | OPA ppm | Total UNK, ppm | Absorbance 333 mu | 350 mu | Co | $R_F/R_P$ MCBA | $R_F/R_P$ MTA | $R_F/R_P$ OPA | $R_F/R_P$ Unk | |
| 3 | 210 | 64 | 952 | 336 | | 33 | 100 | 0.94 | 0.57 | 16 | 5.76 | 39 | | 3.02 | 68 |
| H | 152 | 70 | 1628 | 651 | | 75 | 220 | 1.27 | 0.74 | 46 | 3.37 | 20 | | 1.37 | 85 |
| J | 212 | 10 | 989 | 309 | | 63 | 137 | 0.97 | 0.56 | 57 | 5.55 | 43 | | 2.21 | 67 |
| K | 152 | 11 | 2580 | 1320 | <0.1 | 78 | 163 | 1.41 | 0.79 | 58 | 2.13 | 10 | 7 | 1.85 | 85 |
| L | 100 | 64 | 3099 | 1997 | | 112 | 217 | 1.58 | 0.90 | 59 | 1.77 | 7 | 5 | 1.39 | 93 |
| M | 130 | 65 | 2751 | 1562 | | 105 | 237 | 1.48 | 0.84 | 46 | 1.99 | 8 | 5 | 1.27 | 89 |

The short residence time of B and F helped to stimulate formation of more tiny particles. The residence time for Control G was adequate, but the lower temperature promoted formation of an excessive proportion of tiny particles. Such discovery of tiny crystal formation at low temperatures was surprising, because prior art crystallization oftentimes used lower temperatures to promote formation of and/or growth of larger particle size.

The feedstock contained aqueous acetic acid plus the following components:

| | |
|---|---|
| Isophthalic acid | about 97% |
| MCBA (meta-carboxy benzaldehyde) | 830 ppm |
| MTA (meta-toluic acid) | 227 ppm |
| TPA (terephthalic acid) | 1.4% |
| OPA (ortho-phthalic acid) | 102 ppm |
| UNK (miscellaneous unknowns) | 432 ppm |

| | |
|---|---|
| MCBA (meta-carboxy benzaldehyde) | 5,488 ppm |
| MTA (meta-toluic acid) | 13,200 ppm |
| TPA (terephthalic acid) | 1.2 |
| OPA (ortho-phthalic acid) | 521 ppm |
| UNK (miscellaneous unknowns) | 302 ppm |
| Cobalt catalyst | 1500 ppm |

The single stage crystallization, using the apparatus of Examples 1 and 2, led to results summarized in Table 3. By a series of preparations it was established that the purification should be conducted at a temperature between 180° and 250° F. for a residence time of from 20 to 120 minutes, the rate of evaporation of solvent being so controlled that during said residence time the concentration of solids in the slurry is increased to above 60%.

EXAMPLE 4

The atmospheric boiling point of acetic acid is about 180° F. and water and solid solutes tend to increase the boiling point. Evaporative crystallization involves the distillation of the solvent to promote crystallization of the solute. By distilling acetic acid from the single stage crystallization zone, acetic acid solvent can be recovered. While maintaining the crystallization zone at its boiling point, the rate of distillation can be increased by increasing the heat input. The evaporation rate can be increased, thereby increasing the percentage of recovery of the isphthalic acid.

A dissolving tank was maintained at about 300° F., and the resulting solution was pumped toward a single stage crystallization zone from which acetic acid was being distilled at about 200° F. at an appropriate pressure. Supplemental agitation of the mixture was achieved by directing a recycle stream through a pump, heater, and agitation jets. Of particular importance, the heat input as the recirculating stream flowed through said heater increased the rate of volatilization of the solvent. If desired, the feedstream can be injected into said recycle stream. A product stream was withdrawn at a rate corresponding in IPA content to the feedstream. The volume rate of such product stream is less than the feedstream volume rate because most of the acetic acid is volatilized during the 40 minute average residence time in the single stage recrystallization zone. The volatilization rate is so controlled that said residence time increases the solids content of the slurry so that at least 60% of the total IPA content is dispersed crystals. The product purity and distribution of particle sizes are both satisfactory.

Attention is called to the importance of maintaining adequate rates of acetic acid volatilization so that the overall recovery of isophthalic acid can be satisfactory. This requires the input of a controlled amount of heat without generating troublesome hot spots in the crystallization zone. Those embodiments of the invention featuring a recirculating stream of liquid permit large amounts of heat to be supplied to the boiling slurry. In some prior art recrystallizers, such recirculating stream is withdrawn and is directed through a pump, which sends the liquid back into the crystallization zone. A plurality of spaced apart injection jets, generally close to the bottom of the crystallization zone may be employed. If desired, the feedstream can be injected into such recirculating stream. The present invention utilizes a stream, which is heated to at least partially compensate for the various dissipations of heat (e.g. heat of evaporation of acetic acid solvent from the crystallization zone) from the crystallization zone. The heating of such stream is desirably just prior to being reinjected through said plurality of injection jets into the boiling slurry. Ordinarily the feedstock is hotter than the crystallization zone, and thus has some role in compensating for such heat dissipations.

Various modifications of the invention are possible without departure from the scope of the appended claims.

The invention claimed is:

1. A process for the purification of isophthalic acid produced by the liquid phase, oxygen-containing gas oxidation of meta-xylene, which purification process comprises;

preparing an aqueous acetic acid solvent consisting from about 90 to 98 percent acetic acid and about 2 percent to about 10 percent water;

preparing in a dissolving zone, a hot solution of impure isophthalic acid derived from said oxidation of meta-xylene, said solution being at a temperature within the range from about 190° F. to about 300° F. while maintaining a superatmospheric pressure minimizing the volatilization of said solvent;

directing a feed stream of said hot solution of impure isophthalic acid into a single crystallization zone at a controlled rate, said single crystallization zone containing a slurry of isophthalic acid crystals dispersed in a solution of isophthalic acid in solvent, said crystallization zone being maintained at a pre-determined crystallization temperature selected within the range from 180° F. to 250° F. to promote crystallization of isophthalic acid in said single crystallization zone, the pressure in the crystallization zone being maintained at a pressure low enough that more than half of the solvent content of said feed stream is quickly distilled to promote evaporative crystallization, whereby a slurry comprising purified isophthalic acid is prepared, the solid particles constituting at least 60% of the isophthalic acid content of said slurry, the residence time of the isophthalic acid in said crystallization zone being controlled to be from about 20 to about 120 minutes, said single crystallization zone promoting formation of an acceptable distribution of particle sizes of crystals of purified isophthalic acid;

recirculating a stream of liquid from the crystallization zone, directing such recirculating stream through a pumping zone and reinjecting said recirculating stream into the crystallization zone in such a manner that throughout most of said crystallization zone there is general uniformity of composition, said recirculating stream being heated in a heating zone to at least partially compensate for the various dissipations of heat from said crystallization zone, and to provide the heat required for significant evaporative crystallization sufficiently complete to provide final product concentration in such single stage crystallization zone;

withdrawing a purified stream from said crystallization zone at a rate correlated with the feed stream rate and volume in said crystallization zone to provide said controlled residence time, said purified stream having at least 60% of its isophthalic acid content as solids suspended as slurried solids in said purified stream, and subjecting said withdrawn purified stream to separation by centrifugation or filtration to provide a stream of filtrate containing dissolved impurities and residual isophthalic acid and an acceptable yield of purified filter cake consisting of crystalline particles of isophthalic acid; and recovering purified isophthalic acid having an acceptable distribution of particle sizes from said purified filter cake.

2. The method of claim 1 in which the temperature of the crystallization zone is less than the temperature in the dissolving zone, whereby crystallization occurs at least in part by reason of such lower temperature.

3. A process for the purification of isophthalic acid produced by the liquid phase, oxygen-containing gas oxidation of meta-xylene, which purification process comprises;

preparing an aqueous acetic acid solvent consisting from about 90 to 98% acetic acid and about 2% to about 10% water;

preparing in a dissolving zone, a hot solution of impure isophthalic acid derived from said oxidation of meta-xylene, said solution being at a temperature within the range from about 190° F. to about 300° F. while maintaining a superatmospheric pressure minimizing the volatilization of said solvent;

directing a feed stream of said hot solution of impure isophthalic acid into a single crystallization zone at a controlled rate, said single crystallization zone containing a slurry being maintained at a predetermined crystallization temperature selected within the range from 180° F. to 250° F. and selected to be at least 10° F. cooler than said dissolving zone, said slurry being subjected to vigorous boiling for volatilizing solvent at a pressure correlated with said crystallization temperature whereby solvent is volatilized from said slurry at a very rapid rate to promote crystallization of isophthalic acid in said single crystallization zone, thereby controlling the composition of said slurry so that said slurry comprises solid particles of purified isophthalic acid constituting at least 60% of the isophthalic acid content of said slurry, the solvent content of said slurry being less than 50% of the solvent content of said feed stream by reason of the rapid volatilization of most of said solvent, the residence time of the isophthalic acid in said crystallization zone being controlled to be from about 20 to about 120 minutes, said residence time promoting formation of an acceptable distribution of particle sizes of crystals of purified isophthalic acid;

withdrawing a purified stream from said crystallization zone at a rate correlated with the feed stream rate and volume in said crystallization zone to provide said controlled residence time, and subjecting said withdrawn purified stream to separation by centrifugation or filtration to provide not only a stream of filtrate containing residual isophthalic acid and dissolved impurities but also a purified filter cake consisting of crystalline particles of isophthalic acid; and, recovering from said filter cake purified isophthalic acid having an acceptable distribution of particle sizes.

4. The method of claim 3 in which a recirculating stream of slurry is withdrawn from the crystallization zone, directed through a pump, and reinjected into the crystallization zone in such a manner that throughout most of said crystallization zone there is a general uniformity of composition.

5. The method of claim 4 in which the stream, prior to being reinjected, is heated to at least partially compensate for the various dissipations of heat from the crystallization zone and to provide the heat required for said vigorous boiling of solvent.

6. A process for the purification of isophthalic acid produced by the liquid phase, oxygen-containing gas oxidation of meta-xylene, which purification process comprises:

preparing an aqueous acetic acid solvent consisting from about 90 to 98% acetic acid and about 2% to about 10% water;

preparing in a dissolving zone, a hot solution of impure isophthalic acid derived from said oxidation of meta-xylene, said solution being at a temperature within the range from about 190° F. to about 300° F. while maintaining a superatmospheric pressure minimizing the volatilization of said solvent;

directing a feed stream of said hot solution of impure isophthalic acid into a single crystallization zone at a controlled rate, said single crystallization zone being maintained at a predetermined crystallization temperature of about 210° F. to promote crystallization of isophthalic acid in said single crystallization zone, the pressure in the crystallization zone being maintained at a pressure low enough that a significant portion of the solvent is distilled to promote evaporative crystallization, whereby a slurry comprising purified isophthalic acid is prepared, the residence time of the isophthalic acid in said crystallization zone being controlled to be about 64 minutes, said residence time promoting formation of an acceptable distribution of particle sizes of crystals of purified isophthalic acid:

recirculating a stream of liquid from the crystallization zone, directing such recirculating stream through a pump, and reinjecting said recirculating stream into the crystallization zone in such a manner that throughout most of said crystallization zone there is general uniformity of composition, heating said recirculating stream to at least partially compensate for the various dissipations of heat from the crystallization zone, and to provide the heat required for significant evaporative crystallization sufficiently complete to provide final product concentration in such single stage crystallization;

withdrawing a purified stream from said crystallization zone at a rate correlated with the feed stream rate and volume in said crystallization zone to provide said controlled residence time, and subjecting said withdrawn purified stream to separation by centrifugation or filtration to provide not only a stream of filtrate containing dissolved impurities and residual isophthalic acid but also an acceptable yield of purified filtrate consisting of crystalline particles of isophthalic acid and;

recovering purified isophthalic acid having an acceptable distribution of particle sizes from said purified filter cake.

7. The method of claim 1 in which said crystallization temperature is about 197° F., and the residence time is about 23 minutes and the yield of purified filter cake is about 73%.

8. The method of claim 1 in which said crystallization temperature is about 206° F., the residence time is about 64 minutes, and the yield of purified filter cake is about 70%.

9. The method of crystallizing an organic compound which consists of the steps of:

preparing a feed solution of said organic compound in an organic solvent at an elevated pressure and temperature;

maintaining a very large volume of a slurry of crystals of said organic compound in a single crystallization zone said slurry having a preselected concentration of said organic compound in solid crystalline form in a particle size distribution, said commercially satisfactory preselected concentration being above 60% and a commercially satisfactory yield in recrystallization, the balance of said organic compound and impurities being dissolved in said solvent as a solution, said slurry consisting of said solid crystals in said solution, agitating said slurry by withdrawing a stream of said slurry from said recrystallization zone and directing said stream through a pumping zone and a heating zone and recirculating the heated stream through a plurality of submerged jets into the recrystallization zone, the turn-over time for recirculating the contents of the recrystallization zone being only a few minutes, the space above said recrystallization zone being adapted for the distillation of said organic solvent from said slurry, whereby evaporative recrystallization at a predetermined temperature occurs, said temperature corresponding to the boiling point of said slurry at a predetermined pressure, said predetermined pressure being selected to provide said preselected concentration in said slurry;

withdrawing from said recrystallization zone a product stream of said slurry as product, said withdrawn stream being subjected to centrifugation or filtration to provide a filtrate corresponding generally to the solution portion of said slurry and to provide a filter cake corresponding generally to said dispersed crystal portion of said slurry;

injecting said feed solution into said recrystallization zone at a location remote from withdrawal of said product stream and at a rate corresponding to the rate of said organic compound being withdrawn in said product stream, the average residence time in the recrystallization zone being controlled to be from about 20 to 120 minutes by controlling the heat input in the heating zone to control the vigorousness of the boiling of the slurry to distill solvent at a rate providing said product concentration during said residence time;

said solvent being an aqueous solution consisting of from about 90 to 98% acetic acid and about 2 percent to about 10% water, said organic compound being isophthalic acid, the temperature of the recrystallization zone being maintained at a temperature selected from 180° F. to 250° F., and said temperature being at least 10° F. cooler than said dissolving zone.

* * * * *